US006979684B1

(12) United States Patent
Kamal et al.

(10) Patent No.: US 6,979,684 B1
(45) Date of Patent: Dec. 27, 2005

(54) PYRROLO[2,1-C][1,4]BENZODIAZEPINE-NAPTHALIMIDE CONJUGATES LINKED THROUGH PIPERAZINE MOIETY AND PROCESS FOR PREPARATION THEREOF

(75) Inventors: Ahmed Kamal, Andhra Pradesh (IN); Ramu Rondla, Andhra Pradesh (IN); Gollpalli Bhasker Ramesh Khanna, Andhra Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/881,729

(22) Filed: Jun. 30, 2004

(51) Int. Cl.⁷ ............... C07D 403/14; A61K 31/5517; A61P 35/00
(52) U.S. Cl. ................... 514/220; 540/496
(58) Field of Search ............... 540/496; 514/220

(56) References Cited

U.S. PATENT DOCUMENTS

| 4,874,863 A | 10/1989 | Brana et al. |
| 5,554,622 A | 9/1996 | Brana et al. |

FOREIGN PATENT DOCUMENTS

| WO | 94/07862 | 4/1994 |
| WO | 01/66545 | 9/2001 |

OTHER PUBLICATIONS

Kamal, A., et al. "Design and Synthesis of C-8 Linked Pyrrolobenzodiazepine-Naphthalimide Hybrids as Anti-Tumour Agents." *Bioorganic & Medicinal Chemistry Letters* (2002) vol. 12, No. 15, pp 1933-1935 XP-002316525.

Kamal, A., et al. "Recent Developments inthe Design, Synthesis and Structure-Activity Relationship Studies of Pyrrolo [2,1-c][1,4] benzodiazepines as DNA-Interactive Antitumour Antibiotics." *Current Medicinal Chemistry-Anti-Cancer Agents* (2002) vol. 2, No. 2, pp 215-254.

Kamal, A., et al. "Synthesis of C-8 Alkylamino Substituted Pyrrolo[2,1-c][1,4]-benzodiazepines as Potential Anti-Cancer Agents." *Bioorganic & Medicinal Chemistry Letters* (2002) vol. 12, No. 15, pp 1917-1919 XP-002316526.

*Primary Examiner*—Bruck Kifle
(74) *Attorney, Agent, or Firm*—Ladas and Parry LLP

(57) ABSTRACT

The present invention relates to novel pyrrolo[2,1-c][1,4] benzodiazepine-napthalimide hybrids linked through piperazine moiety as potential antitumour agents. The present invention also relates to a process for the preparation of novel pyrrolo[2,1-c][1,4]benzodiazepine-napthalimide hybrids linked through piperazine moiety useful as potential antitumour agents.

22 Claims, No Drawings

PYRROLO[2,1-C][1,4]BENZODIAZEPINE-NAPTHALIMIDE CONJUGATES LINKED THROUGH PIPERAZINE MOIETY AND PROCESS FOR PREPARATION THEREOF

FIELD OF THE INVENTION

The present invention relates to novel pyrrolo[2,1-c][1,4] benzodiazepine-napthalimide hybrids linked through piperazine moiety as potential antitumour agents. The present invention also relates to a process for the preparation of novel pyrrolo[2,1-c][1,4]benzodiazepine-napthalimide hybrids linked through piperazine moiety useful as potential antitumour agents.

The present invention particularly relates to the synthesis of pyrrolo[2,1-c][1,4]benzodiazepine-napthalimide hybrids linked through piperazine moiety as possible anticancer agents. The structural formula of novel pyrrolo[2,1-c][1,4] benzodiazepine-napthalimide hybrids (VIII) is as follows, wherein $n_1$=2, 3, 4, $n_2$ =2, 3, 4.

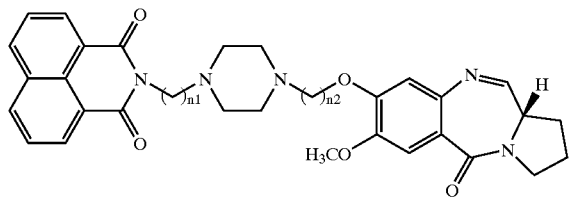

VIII

BACKGROUND OF THE INVENTION

Pyrrolo[2,1-c][1,4]benzodiazepines are a family of DNA interactive antitumour antibiotics derived from *Streptomyces* species. Examples of naturally occurring pyrrolo[2,1-c][1,4]benzodiazepines include anthramycin, tomaymycin, sibiromycin and DC-81. These compounds show their biological activity through covalent binding via their N10-C11 imine/carbinol amine moiety to the C2-amine position of a guanine residue within the minor groove of DNA giving rise to the preference for Pu-G-Pu sequences. (Kunimoto, S.; Masuda, T.; Kanbayashi, N.; Hamada, M.; Naganawa, H.; Miyamoto, M.; Takeuchi, T and Unezawa, H. *J. Antibiot.,* 1980, 33, 665.; Kohn, K. W. and Speous, C. L. *J. Mol. Biol.,* 1970, 91, 551.; Hurley, L. H.; Gairpla, C. and Zmijewski, M. *Biochem. Biophy. Acta.,* 1977, 475, 521.; Kaplan, D. J. and Hurley, L. H. *Biochemistry,* 1981, 20, 7572.) The molecules have a right-handed twist, when viewed from the C-ring towards the A-ring. This enables the PBD to mirror the curvature of B-form DNA and maintain isohelical contact with the walls and floor of the minor groove. In the last few years a growing interest has been shown in the development of new pyrrolo[2,1-c][1,4]benzodiazepine hybrids. Many PBD conjugates have been synthesized and investigated for their anticancer activity (Thurston, D. E.; Morris, S. J.; Hartley, J. A. *Chem. Commun.* 1996, 563.; Damayanthi, Y.; Reddy, B. S. P.; Lown, J. W. *J. Org. Chem.* 1999, 64, 290.; Kamal, A.; Reddy, B. S. N.; Reddy, G. S. K.; Ramesh, G *Bioorg. Med. Chem. Lett.* 2002, 12, 1933, Kamal, A.; Reddy, B. S. N.; Reddy Indian patent application No. 209/DEL/2000). Recently C-8 linked PBD dimers with C2/C2 exounsaturation have been designed and synthesized (Gregson, S. J.; Howard, P. W.; Hartley, J. A.; Brooks, N. A.; Adam, L. J.; Jenkins, T. C.; Kelland, L. R. and Thurston, D. E., *J. Med. Chem.* 2001, 44, 737). Also, non cross-linking mixed imine-amide PBD dimers have been synthesized that have significant DNA binding ability and potent antitumor activity (Kamal, A.; Ramesh, G.; Laxman, N.; Ramulu, P.; Srinivas, O.; Neelima, K.; Kondapi, A. K.; Srinu, V. B.; Nagarajaram, H. M. *J. Med. Chem.* 2002, 45, 4679). During earlier studies in this laboratory PBDs have been linked to naphthalimides through alkane chain which have shown promising anticancer activity (Kamal, A.; Reddy, B. S. N.; Reddy, G. S. K.; Ramesh, G *Bioorg. Med. Chem. Lett.* 2002, 12, 1933, Kamal, A.; Reddy, B. S. N.; Reddy Indian patent application No. 209/DEL/2000). However, in the present invention the PBD and naphthalimide moieties have been linked through piperazine moiety with alkyl side arms, instead of simple alkane chain spacers. By incorporation of a piperazine moiety in the spacer these new hybrids not only exhibit enhanced in vitro anticancer activity but remarkable DNA binding affinity for a number of this type of hybrids as illustrated in Table 1 and 2.

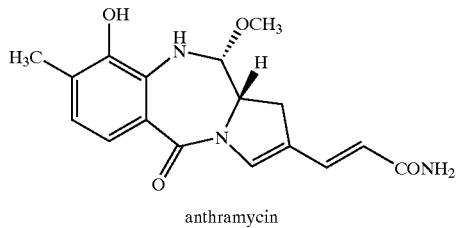

anthramycin

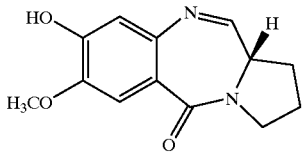

DC-81

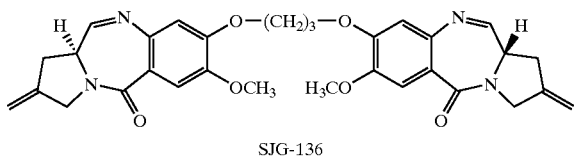

SJG-136

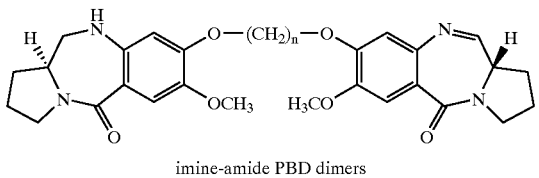

imine-amide PBD dimers

OBJECTS OF THE INVENTION

The main objective of the present invention is to provide new pyrrolo[2,1-c][1,4]benzodiazepines useful as anticancer agents. Another objective of the present invention is to provide a process for the preparation of novel pyrrolo[2,1-c][1,4]benzodiazepines useful as antitumor agents.

SUMMARY OF THE INVENTION

Accordingly, the present invention provides a novel pyrrolo[2,1-c][1,4]benzodiazepines of formula VIII where $n_1$=2, 3, 4, $n_2$=2, 3, 4.

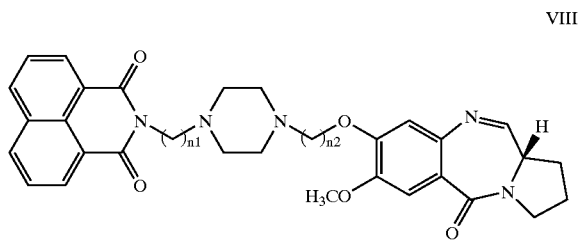

VIII

The present invention also provides a process for the preparation of pyrrolo[2,1-c][1,4]benzodiazepines of formula VIII shown above where $n_1$=2, 3, 4, $n_2$=2, 3, 4, which comprises of reacting (2S)-N-[4-hydroxy-5-methoxy-2-nitrobenzoyl]pyrrolidine-2-carboxaldehyde diethyl thioacetal of formula IV with dibromoalkanes in an aprotic water miscible organic solvent in the presence of a mild inorganic base at refluxing temperature for a period of 48 h, isolating 2-S-N-[4-(n-bromo alkoxy)-5-methoxy-2-nitrobenzoyl]pyrrolidine-2-carbaxaldehyde diethyl thioacetal of formula V, reacting the compound of formula V with piperazine attached naphthalimide in presence of mild inorganic bases isolating compound of formula VI, reducing it with $SnCl_2.2H_2O$ in presence of organic solvent at a reflux temperature, reacting the above amino compound of formula VII with known deprotecting agents in a conventional manner to give novel pyrrol[2,1-c][1,4]benzodiazepine of formula VIII wherein n is as stated above.

DETAILED DESCRIPTION OF THE INVENTION

The precursor, (2S)-N-[4-hydroxy-5-methoxy-2-nitrobenzoyl]pyrrolidine-2-carboxaldehyde diethylthioacetal of formula IV (Thurston, D. E.; Murthy, V. S.; Langley, D. R.; Jones, G.; B. Synthesis, 1990, 81) has been prepared by literature methods.

Some representative compounds of formula VIII of present invention are given below:

1. 7-Methoxy-8-{2-[4-[2-(1,3-dioxo-benz[de]isoquinolin-2-yl)ethyl]piperazin-1-yl]ethyl}-oxy-(11aS)-1,2,3,11a tetrahydro-5H-pyrrolo[2,1-c][1,4]benzodiazepin-5-one
2. 7-Methoxy-8-{3-[4-[2-(1,3-dioxo-benz[de]isoquinolin-2-yl)ethyl]piperazin-1-yl]propyl}-oxy-(11aS)-1,2,3,11a tetrahydro-5H-pyrrolo[2,1-c][1,4]benzodiazepin-5-one
3. 7-Methoxy-8-{4-[4-[2-(1,3-dioxo-benz[de]isoquinolin-2-yl)ethyl]piperazin-1-yl]butyl}-oxy-(11aS)-1,2,3,11a tetrahydro-5H-pyrrolo[2,1-c][1,4]benzodiazepin-5-one
4. 7-Methoxy-8-{3-[4-[3-(1,3-dioxo-benz[de]isoquinolin-2-yl)propyl]piperazin-1-yl]propyl}-oxy-(11aS)-1,2,3,11a tetrahydro-5H-pyrrolo[2,1-c][1,4]benzodiazepin-5-one
5. 7-Methoxy-8-{4-[4-[4-(1,3-dioxo-benz[de]isoquinolin-2-yl)butyl]piperazin-1-yl]butyl}-oxy-(11aS)-1,2,3,11a tetrahydro-5H-pyrrolo[2,1-c][1,4]benzodiazepin-5-one These new analogues of pyrrolo[2,1-c][1,4]benzodiazepine hybrids have shown promising anticancer activity in in selected human cancer cell lines of colon (HT-29, HCT-15), lung (A-549, HOP-62), cervix (SiHa) origin. The molecules synthesized are of immense biological significance with potential sequence selective DNA-binding property. This resulted in design and synthesis of new congeners as illustrated in Scheme-I which comprises of 1. The ether linkage at C-8 position of DC-81 intermediates with napthalimide moiety.
2. Refluxing the reaction mixture for 24–48 h.
3. Synthesis of C-8 linked PBD hybrids.
4. Purification by column chromatography using different solvents like ethyl acetate, hexane, dichloromethane and methanol.

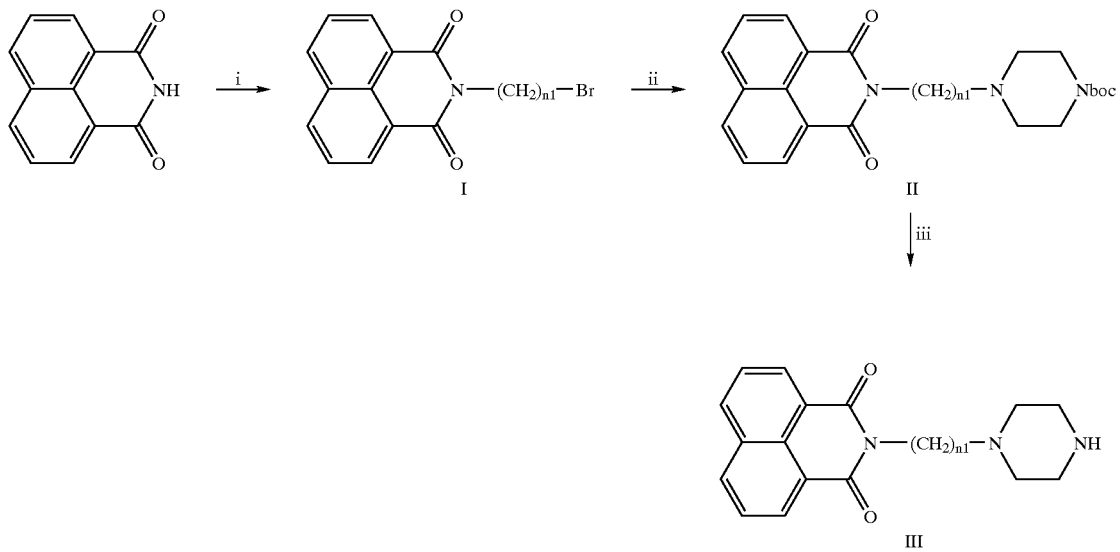

$n_1$ = 2, 3, 4

Reagents and Conditions (i) Dibromo alkanes, $K_2CO_3$, acetonitrile, reflux, 12 h; (ii) N-Boc piperazine, $K_2CO_3$, acetonitrile, reflux, 8 h; (iii) $CF_3COOH$, $CHCl_3$, r.t., 12 h.

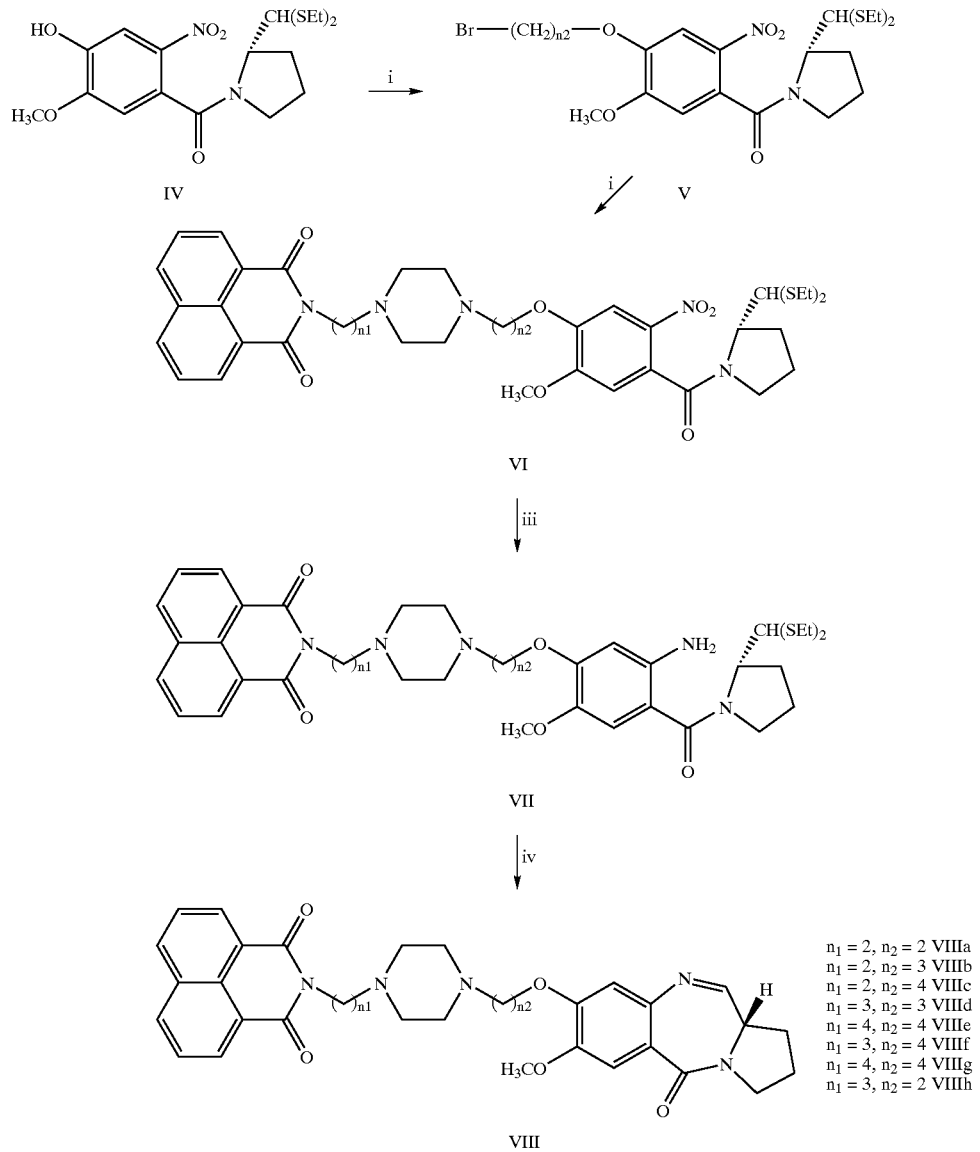

Reagents and Conditions (i) Dibromo alkanes, $K_2CO_3$, acetonitrile, reflux, 24 h; (ii) compound I, $K_2CO_3$, acetonitrile, reflux, 12 h; (iii) $SnCl_2$·$2H_2O$, methanol, reflux, 5 h; (iv) $HgCl_2$, $CaCO_3$, acetonitrile/$H_2O$, r.t., 12 h.

The following examples are given by way of illustration and therefore should not be construed to the present limit of the scope of invention.

Example 1

To a solution of (2S)-N-[4-hydroxy-5-methoxy-2-nitrobenzoyl]pyrrolidine-2-carboxaldehyde diethyl thioacetal of formula IV (800 mg, 2 mmol) in acetone were added anhydrous $K_2CO_3$ (829 mg, 6 mmol) and 1,2 dibromo ethane (940 mg, 5 mmol) and the mixture was refluxed for 48 h. After completion of reaction $K_2CO_3$ was removed by filtration and the solvent was evaporated under redused pressure, purification by column chromatography afforded compound V.

$^1$H NMR (CDCl$_3$) 1.30–1.45 (m, 6H), 1.70–2.35 (m, 4H), 2.70–2.85 (m, 4H), 3.12–3.30 (m, 2H), 3.70 (t, 2H, J=6.3 Hz), 3.95 (s, 3H), 4.40 (t, 2H, J=6 Hz), 4.60–4.75 (m, 1H), 4.82 (d, 1H, J=4.3 Hz), 6.80 (s, 1H), 7.65 (s, 1H).

To a solution of 2S-N-[4-(2-bromo ethoxy)-5-methoxy-2-nitrobenzoyl]pyrrolidine-2-carbaxaldehyde diethyl thioacetal of formula V (507 mg, 1 mmol), piperazine attached naphthalimide (340 mg, 1.1 mmol) in acetone was added anhydrous $K_2CO_3$ (415 mg, 3 mmol) and the mixture was refluxed for 24 h. After completion of reaction $K_2CO_3$ was removed by filtration and the solvent was evaporated under reduced pressure, purification by column chromatography afforded compound VI.

$^{1}$H NMR (CDCl$_3$, 200 MHz) 1.22–1.40 (m, 6H), 1.70–2.35 (m, 4H), 2.55–2.95 (m, 16H), 3.15–3.32 (m, 2H), 3.92 (s, 3H), 4.15–4.35 (m, 4H), 4.57–4.72 (m, 1H), 4.80 (d, 1H, J=4.3 Hz), 6.77 (s, 1H), 7.60–7.80 (m, 3H), 8.30 (t, 2H, J=8 Hz), 8.55 (d, 2H, J=7.6 Hz).

To a solution of 2S-N-{4-[2-[4-[2-(1,3-dioxo-benz[de]isoquinolin-2-yl)ethyl]piperazin-1-yl]ethyl]-oxy-5-methoxy-2-nitrobenzoyl}pyrrolidine-2-carbaxaldehyde diethyl thioacetal of formula VI (736 mg, 1 mmol) in methanol was added SnCl$_2$.2H$_2$O (1.12 gr, 5 mmol) and the mixture was refluxed until the TLC indicated the completion of reaction. Methanol was evaporated and 10% NaHCO$_3$ solution was added. Aqueous layer was extracted with ethyl acetate, combined organic phases were dried over Na$_2$SO$_4$ and evaporated under vacuum to afford amino thioacetal (VII) and directly used in the next step.

A solution of VII (706 mg, 1 mmol) HgCl$_2$ (624 mg, 2.3 mmol) and CaCO$_3$ (250 mg, 2.5 mmol) in CH$_3$CN—H$_2$O (4:1) was stirred at room temperature until the TLC indicated complete consumption of the starting material. The reaction mixture was diluted with ethyl acetate and filtered through a celite bed. The organic layer was concentrated, dried and purified by column chromatography to give the compound VIII.

$^{1}$H NMR (CDCl$_3$, 200 MHz) 1.90–2.40 (m, 4H), 2.45–2.92 (m, 12H), 3.55–3.82 (m, 3H), 3.92 (s, 3H), 4.05–4.40 (m, 4H), 6.77 (s, 1H), 7.45 (s, 1H), 7.62 (d, 1H, J=4.39 Hz), 7.76 (t, 2H, J=7.69 Hz), 8,20 (d, 2H, J=8.2 Hz), 8.60 (d, 2H, J=7.32 Hz).

Example 2

To a solution of (2S)-N-[4-hydroxy-5-methoxy-2-nitrobenzoyl]pyrrolidine-2-carbaxaldehyde diethyl thioacetal of formula IV (800 mg, 2 mmol) in acetone were added anhydrous K$_2$CO$_3$ (828 mg, 6 mmol) and 1,3 dibromo propane (1 gr, 5 mmol) and the mixture was refluxed for 48 h. After completion of reaction K$_2$CO$_3$ was removed by filtration and the solvent was evaporated under reduced pressure, purification by column chromatography afforded compound V.

$^{1}$H NMR (CDCl$_3$, 200 MHz) 1.25–1.40 (m, 6H), 1.72–2.42 (m, 6H), 2.70–2.8 (m, 4H), 3.15–3.30 (m, 2H), 3.60 (t, 2H, J=6.20 Hz), 3.95 (s, 3H), 4.20 (t, 2H, J=4.96 Hz), 4.60–4.75 (m, 1H), 4.82 (d, 1H, J=4.33 Hz), 6.78 (s, 1H), 7.68 (s, 1H).

To a solution of 2S-N-[4-(3-bromo propoxy)-5-methoxy-2-nitrobenzoyl]pyrrolidine-2-carbaxaldehyde diethyl thioacetal of formula V (521 mg, 1 mmol), piperazine attached naphthalimide (340 mg, 1.1 mmol) in acetone was added anhydrous K$_2$CO$_3$ (415 mg, 3 mmol) and the mixture was refluxed for 24 h. After completion of reaction K$_2$CO$_3$ was removed by filtration and the solvent was evaporated under reduced pressure, purification by column chromatography afforded compound VI.

$^{1}$H NMR (CDCl$_3$, 200 MHz) 1.30–1.42 (m, 6H), 1.70–2.30 (m, 6H), 2.40–2.82 (m, 16H), 3.15–3.30 (m, 2H), 3.92 (s, 3H), 4.15 (m, 2H), 4.30 (m, 2H), 4.60–4.70 (m, 1H), 4.82 (d, 1H, J=4.25 Hz), 6.75 (s, 1H), 7.65 (s, 1H), 7.75 (t, 2H, J=7.4 Hz), 8.2 (d, 2H, J=8 Hz), 8.6 (d, 2H, J=7.6 Hz).

To a solution of 2S-N-{4-[3-[4-[2-(1,3-dioxo-benz[de]isoquinolin-2-yl)ethyl]piperazin-1-yl]propyl]-oxy-5-methoxy-2-nitrobenzoyl}pyrrolidine-2-carbaxaldehyde diethyl thioacetal of formula VI (750 mg, 1 mmol) in methanol was added SnCl$_2$.2H$_2$O (1.12 gr, 5 mmol) and the mixture was refluxed until the TLC indicated the completion of reaction. Methanol was evaporated and 10% NaHCO$_3$ solution was added. Aqueous layer was extracted with ethyl acetate. Combined organic phases were dried over Na$_2$SO$_4$ and evaporated under vacuum to afford amino thioacetal (VII) and directly used in the next step.

A solution of VII (720 mg, 1 mmol) HgCl$_2$ (624 mg, 2.3 mmol) and CaCO$_3$ (250 mg, 2.5 mmol) in CH$_3$CN—H$_2$O (4:1) was stirred at room temperature until the TLC indicated complete consumption of the starting material. The reaction mixture was diluted with ethyl acetate and filtered through a celite bed. The organic layer was concentrated, dried and purified by column chromatography to give the compound VIII.

$^{1}$H NMR (CDCl$_3$, 200 MHz) 1.60–2.16 (m, 6H), 2.25–2.80 (m, 12H), 3.50–3.82 (m, 3H), 3.95 (s, 3H), 4.05–4.40 (m, 4H), 6.80 (s, 1H), 7.45 (s, 1H), 7.62 (d, 1H, J=3.33 Hz), 7.79 (t, 2H, J=7.32 Hz), 8.20 (d, 2H, J=8.05 Hz), 8.60 (d, 2H, J=7.32 Hz).

Example 3

To a solution of (2S)-N-[4-hydroxy-5-methoxy-2-nitrobenzoyl]pyrrolidine-2-carboxaldehyde diethyl thioacetal of formula (800 mg, 2 mmol) in acetone were added anhydrous K$_2$CO$_3$ (829 mg, 6 mmol) and 1,4 dibromo butane (1.07 gr, 5 mmol) and the mixture was refluxed for 48 h. After completion of reaction K$_2$CO$_3$ was removed by filtration and the solvent was evaporated under redused pressure, purification by column chromatography afforded compound V.

$^{1}$H NMR (CDCl$_3$, 300 MHz) 1.30–1.40 (m, 6H), 1.75–2.40 (m, 8H), 2.70–2.85 (m, 4H), 3.15–3.30 (m, 2H), 3.50 (t, 2H, J=6.25 Hz), 3.95 (s, 3H), 4.10 (m, 2H), 4.60–4.70 (m, 1H), 4.82 (d, 1H, J=4.3 Hz), 6.75 (s, 1H), 7.62 (s, 1H).

To a solution of 2S-N-[4-(4-bromo butoxy)-5-methoxy-2-nitrobenzoyl]pyrrolidine-2-carbaxaldehyde diethyl thioacetal of formula V (535 mg, 1 mmol), piperazine attached naphthalimide (340 mg, 1.1 mmol) in acetone was added anhydrous K$_2$CO$_3$ (415 mg, 3 mmol) and the mixture was refluxed for 24 h. After completion of reaction K$_2$CO$_3$ was removed by filtration and the solvent was evaporated under redused pressure, purification by column chromatography afforded compound VI.

$^{1}$H NMR (CDCl$_3$, 200 MHz) 1.25–1.40 (m, 6H), 1.60–2.15 (m, 8H), 2.35–2.85 (m, 16H), 3.15–3.30 (m, 2H), 3.92 (s, 3H), 4.12 (m, 1H), 4.30 (m, 2H), 4.60–4.72 (m, 1H), 4.80 (d, 1H, J=4.23 Hz), 6.75 (s, 1H), 7.60 (s, 1H), 7.75 (t, 2H, J=7.45 Hz), 8.2 (d, 2H, J=8.25 Hz), 8.56 (d, 2H, J=7.62 Hz).

To a solution of 2S-N-{4-[4-[2-(1,3-dioxo-benz[de]isoquinolin-2-yl)ethyl]piperazin-1-yl]butyl]-oxy-5-methoxy-2-nitrobenzoyl}pyrrolidine-2-carbaxaldehyde diethyl thioacetal (764 mg, 1 mmol) of formula VI in methanol was added SnCl$_2$.2H$_2$O (1.12 gr, 5 mmol) and the mixture was refluxed until the TLC indicated the completion of reaction. The methanol was evaporated and 10% NaHCO$_3$ solution was added. The aqueous layer was extracted with ethyl acetate, the combined organic phases were dried over Na$_2$SO$_4$ and evaporated under vacuum to afford the amino thioacetal (VII) and directly used in the next step.

A solution of VII (734 mg, 1 mmol) HgCl$_2$ (624 mg, 2.3 mmol) and CaCO$_3$ (250 mg, 2.5 mmol) in CH$_3$CN—H$_2$O (4:1) was stirred at room temperature until the TLC indicated complete consumption of the starting material. The reaction mixture was diluted with ethyl acetate and filtered through a celite bed. The organic layer was concentrated, dried and purified by column chromatography to give the compound VIII.

$^1$H NMR (CDCl$_3$, 200 MHz) 1.56–2.15 (m, 8H), 2.25–2.80 (m, 16H), 3.45–3.82 (m, 3H), 3.92 (s, 3H), 4.0–4.15 (m, 2H), 4.22–4.37 (t, 2H), 6.70 (s, 1H), 7.42 (s, 1H), 7.60 (d, 1H, J=4.25 Hz), 7.72 (t, 2H, J=7.4 Hz), 8.16 (d, 2H, J=8.1 Hz), 8.56 (d, 2H, J=7.42 Hz).

Example 4

To a solution of (2S)-N-[4-hydroxy-5-methoxy-2-nitrobenzoyl]pyrrolidine-2-carboxaldehyde diethyl thioacetal of formula IV (800 mg, 2 mmol) in acetone were added anhydrous K$_2$CO$_3$ (829 mg, 6 mmol) and 1,3 dibromo propane (1 gr, 5 mmol) and the mixture was refluxed for 48 h. After completion of reaction K$_2$CO$_3$ was removed by filtration and the solvent was evaporated under redused pressure, purification by column chromatography afforded compound V.

$^1$H NMR (CDCl$_3$, 200 MHz) 1.25–1.40 (m, 6H), 1.72–2.42 (m, 6H), 2.70–2.8 (m, 4H), 3.15–3.30 (m, 2H), 3.60 (t, 2H, J=6.20 Hz), 3.95 (s, 3H), 4.20 (t, 2H, J=4.96 Hz), 4.60–4.75 (m, 1H), 4.82 (d, 1H, J=4.33 Hz), 6.78 (s, 1H), 7.68 (s, 1H).

To a solution of 2S-N-[4-(3-bromo propoxy)-5-methoxy-2-nitrobenzoyl]pyrrolidine-2-carbaxaldehyde diethyl thioacetal of formula V (521 mg, 1 mmol), piperazine attached naphthalimide (324 mg, 1 mmol) in acetone were added anhydrous K$_2$CO$_3$ (415 mg, 3 mmol) and the mixture was refluxed for 24 h. After completion of reaction K$_2$CO$_3$ was removed by filtration and the solvent was evaporated under reduced pressure, purification by column chromatography afforded compound VI.

$^1$H NMR (CDCl$_3$, 200 MHz) 1.25–1.42 (m, 6H), 1.70–2.40 (m, 8H), 2.60–3.30 (m, 18H), 3.92 (s, 3H), 4.05 (m, 4H), 4.70–4.80 (m, 1H), 4.82 (d, 1H, J=4.25 Hz), 6.77 (s, 1H), 7.60 (s, 1H), 7.75 (t, 2H, J=7.35 Hz), 8.18 (d, 2H, J=8 Hz), 8.55 (d, 2H, J=7.55 Hz).

To a solution of 2S-N-{4-[3-[3-[4-[3-(1,3-dioxo-benz[de] isoquinolin-2-yl)propyl]piperazin-1-yl]propyl]-oxy-5-methoxy-2-nitrobenzoyl}pyrrolidine-2-carbaxaldehyde diethyl thioacetal of formula VI (764 mg, 1 mmol) in methanol was added SnCl$_2$.2H$_2$O (1.12 gr, 5 mmol) and the mixture was refluxed until the TLC indicated the completion of reaction. The methanol was evaporated and 10% NaHCO$_3$ solution was added. The aqueous layer was extracted with ethyl acetate, the combined organic phases were dried over Na$_2$SO$_4$ and evaporated under vacuum to afford the amino thioacetal (VII) and directly used in the next step.

A solution of VII (734 mg, 1 mmol) HgCl$_2$ (624 mg, 2.3 mmol) and CaCO$_3$ (250 mg, 2.5 mmol) in CH$_3$CN—H$_2$O (4:1) was stirred at room temperature until the TLC indicated complete consumption of the starting material. The reaction mixture was diluted with ethyl acetate and filtered through a celite bed. The organic layer was concentrated, dried and purified by column chromatography to give the compound VIII.

$^1$H NMR (CDCl$_3$, 200 MHz) 1.75–2.18 (m, 8H), 2.22–2.80 (m, 16H), 3.45–4.30 (m, 10OH), 6.75 (s, 1H), 7.45 (s, 1H), 7.60 (d, 1H, J=4.2 Hz), 7.72 (t, 2H, J=7.4 Hz), 8.20 (d, 2H, J=8.1 Hz), 8.58 (d, 2H, J=7.35 Hz).

Example 5

To a solution of (2S)-N-[4-hydroxy-5-methoxy-2-nitrobenzoyl]pyrrolidine-2-carboxaldehyde diethyl thioacetal of formula IV (800 mg, 2 mmol) in acetone were added anhydrous K$_2$CO$_3$ (829 mg, 6 mmol) and 1,4 dibromo butane (1 gr, 5 mmol) and the mixture was refluxed for 48 h. After completion of reaction K$_2$CO$_3$ was removed by filtration and the solvent was evaporated under redused pressure, purification by column chromatography afforded compound V.

$^1$H NMR (CDCl$_3$, 300 MHz) 1.30–1.40 (m, 6H), 1.75–2.40 (m, 8H), 2.70–2.85 (m, 4H), 3.15–3.30 (m, 2H), 3.50 (t, 2H, J=6.25 Hz), 3.95 (s, 3H), 4.10 (m, 2H), 4.60–4.70 (m, 1H), 4.82 (d, 1H, J=4.3 Hz), 6.75 (s, 1H), 7.62 (s, 1H).

To a solution of 2S-N-[4-(4-bromo butoxy)-5-methoxy-2-nitrobenzoyl]pyrrolidine-2-carbaxaldehyde diethyl thioacetal of formula V (538 mg, 1 mmol), piperazine attached naphthalimide (337 mg, 1 mmol) in acetone were added anhydrous K$_2$CO$_3$ (415 mg, 3 mmol) and the mixture was refluxed for 24 h. After completion of reaction K$_2$CO$_3$ was removed by filtration and the solvent was evaporated under reduced pressure, purification by column chromatography afforded compound VI.

$^1$H NMR (CDCl$_3$, 200 MHz) 1.60–2.33 (m, 12H), 2.52–3.0 (m, 16H), 3.12–3.30 (m, 2H), 3.95 (s, 1H), 4.02–4.25 (m, 4H), 4.60–4.72 (m, 1H), 4.80 (d, 1H, J=4.3 Hz), 6.75 (s, 1H), 7.60 (s, 1H), 7.75 (t, 2H, J=7.45 Hz), 8.18 (d, 2H, J=8.2 Hz), 8.56 (d, 2H, J=7.6 Hz).

To a solution of 2S-N-{4-[4-[4-[4-(1,3-dioxo-benz[de] isoquinolin-2-yl)butyl]piperazin-1-yl]butyl]-oxy-5-methoxy-2-nitrobenzoyl}pyrrolidine-2-carbaxaldehyde diethyl thioacetal (792 mg, 1 mmol) of formula VI in methanol was added SnCl$_2$.2H$_2$O (1.12 gr, 5 mmol) and the mixture was refluxed until the TLC indicated the completion of reaction. The methanol was evaporated and 10% NaHCO$_3$ solution was added. The aqueous layer was extracted with ethyl acetate, the combined organic phases were dried over Na$_2$SO$_4$ and evaporated under vacuum to afford amino thioacetal (VII) and directly used in the next step.

A solution of VII (762 mg, 1 mmol) HgCl$_2$ (624 mg, 2.3 mmol) and CaCO$_3$ (250 mg, 2.5 mmol) in CH$_3$CN—H$_2$O (4:1) was stirred at room temperature until the TLC indicated complete consumption of the starting material. The reaction mixture was diluted with ethyl acetate and filtered through a celite bed. The organic layer was concentrated, dried and purified by column chromatography to give the compound VIII.

$^1$H NMR (CDCl$_3$, 300 MHz) 1.50–2.10 (m, 12H), 2.25–2.80 (m, 16H), 3.45–4.30 (m, 10H), 6.75 (s, 1H), 7.45 (s, 1H), 7.62 (d, 1H, J=4.2 Hz), 7.75 (t, 2H, J=7.3 Hz), 8.20 (d, 2H, J=8.1 Hz), 8.56 (d, 2H, J=7.40 Hz).

Biological Activity:

In vitro cytotoxicity against human cancer cell lines: The human cancer cell lines procured from National Cancer Institute, Frederick, U.S.A or National Center for Cell Science; Pune, India. were used in present study. Cells were grown in tissue culture flasks in complete growth medium (RPMI-1640 medium with 2 mM glutamine, 100 µg/ml streptomycin, pH 7.4, sterilized by filtration and supplemented with 10% fetal calf serum and 100 units/ml penicillin before use) at 37° C. in an atmosphere of 5% CO$_2$ and 90% relative humidity in a carbon dioxide incubator. The cells at subconfluent stage were harvested from the flask by treatment with trypsin (0.5% in PBS containing 0.02% EDTA) for determination of cytotoxicity. Cells with viability of more than 98% as determined by trypan blue exclusion were used for assay. The cell suspension of the required cell density were prepared in complete growth medium with gentamycin (50 µg/ml) for determination of cytotoxicity.

A stock solutions of ($2 \times 10^{-2}$ M) of test material were prepared in DMSO. The stock solutions were serially diluted with complete growth medium containing 50 µg/ml of gentamycin to obtain working test solutions of required concentrations.

In vitro cytotoxicity against human cancer cell lines was determined (Monks, A., Scudiero, D., Skehan, P, Shoemaker R., Paull, K., Vistica, D., Hose, C., Langley, J., Cronise, P., Vaigro-Wolff, A., Gray-Goodrich, M., Campbell, H., Mayo, J and Boyd M. *J. Natl. Cancer Inst.*, 1991, 83, 757–766) using 96-well tissue culture plates. The 100 µl of cell suspension was added to each well of the 96-well tissue culture plate. The cells were incubated for 24 hours. Test materials in complete growth medium (100 µl) were added after 24 hours incubation to the wells containing cell suspension. The plates were further incubated for 48 hours (at 37° C. in an atmosphere of 5% and 90% relative humidity in a carbon dioxide incubator) after addition of test material and then the cell growth was stopped by gently layering trichloroacetic acid (TCA, 50 µl, 50%) on top of the medium in all the wells. The plates were incubated at 4° C. for one hour to fix the cells attached to the bottom of the wells. The liquid of all the wells was gently pipetted out and discarded. The plates were washed five times with distilled water to remove TCA, growth medium low molecular weight metabolites, serum proteins etc and air-dried. Cell growth was measured by staining with sulforhodamine B dye (Skehan et al., 1990). The adsorbed dye was dissolved in Tris-Buffer (100 ml, 0.01 M, pH 10.4) and plates were gently stirred for 5 minutes on a mechanical stirrer. The optical density was recorded on ELISA reader at 540 nm.

The cell growth was calculated by subtracting mean OD value of respective blank from the mean OD value of experimental set. Percent growth in presence of test material was calculated considering the growth in absence of any test material as 100% and in turn percent growth inhibition in presence of test material will be calculated.

Cytotoxicity:

Compounds were evaluated for the primary anticancer activity. The cytotoxicity data for some representative compounds has shown in Table 1.

TABLE 2

DNA Thermal Denaturation Studies:

| Compound | Induced $\Delta T_m$ ° C. after incubation at 37° C. | |
|---|---|---|
|  | 0 h | 18 h |
| VIIIa | 21.9 | 22.7 |
| VIIIb | 25.8 | 26.7 |
| VIIIc | 23.4 | 24.2 |
| VIIId | 13.1 | 14.3 |
| VIIIe | 20.9 | 21.7 |
| DC-81 | 0.3 | 0.7 |

For CT-DNA alone at pH 7.00±0.01, $T_m$=69.8° C.±0.01 (mean value from 10 separate determinations), all $\Delta T_m$ values are ±0.1–0.2° C. For a 1:5 molar ratio of [PBD]/[DNA], where CT-DNA concentration=100 µM and ligand concentration=20 µM in aqueous sodium phosphate buffer [10 mM sodium phosphate+1 mM EDTA, pH 7.00±0.01].

We claim:

1. A compound of formula VIII where $n_1$ is 2, 3, or 4, and $n_2$ is 2, 3, or 4

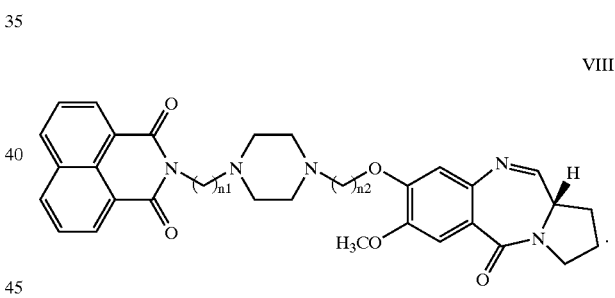

VIII 2. 7-Methoxy-8-{2-[4-[2-(1,3-dioxo-benz[de]isoquinolin-2-yl)alkyl]piperazin-1-yl]alkyl}-oxy-(11aS)-1,2,3,11a tetrahydro-5H-pyrrolo[2,1-c][1,4]benzodiazepin-5-one of formula VIII where $n_1$ is 2, 3 or 4 and $n_2$ is 2, 3 or 4

TABLE 1

The percentage growth inhibition data for napthalimide-PBD hybrids

| | Cancer cell lines | | | | | | | | | | | | | | |
|---|---|---|---|---|---|---|---|---|---|---|---|---|---|---|---|
| Compd | HT-29 | | | HCT-15 | | | A-549 | | | HOP-62 | | | SiHa | | |
| (mol/L) | $10^{-4}$ | $10^{-5}$ | $10^{-6}$ | $10^{-4}$ | $10^{-5}$ | $10^{-6}$ | $10^{-4}$ | $10^{-5}$ | $10^{-6}$ | $10^{-4}$ | $10^{-5}$ | $10^{-6}$ | $10^{-4}$ | $10^{-5}$ | $10^{-6}$ |
| VIIIb | 88 | 85 | 91 | a | 59 | 58 | 88 | a | a | a | 86 | 72 | a | 44 | 54 |
| VIIIc | 94 | 86 | 80 | a | 69 | 60 | 95 | a | a | a | 93 | 86 | 56 | 39 | a |
| VIIId | 95 | 62 | 63 | a | a | a | 95 | 30 | 51 | 78 | a | a | 85 | 65 | 31 |
| VIIIe | 92 | 78 | 67 | a | 62 | 59 | 93 | a | a | a | 93 | 80 | 42 | 40 | 44 | a: not tested

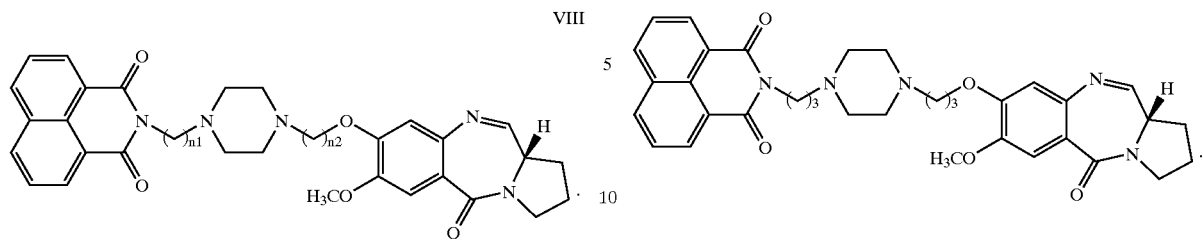

VIII 3. 7-Methoxy-8-{2-[4-[2-(1,3-dioxo-benz[de]isoquinolin-2-yl)ethyl]piperazin-1-yl]ethyl}-oxy-(11aS)-1,2,3,11a tetrahydro-5H-pyrrolo[2,1-c][1,4]benzodiazepin-5-one of the structural formula

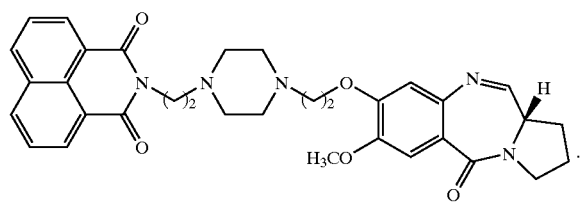

4. 7-Methoxy-8-{3-[4-[2-(1,3-dioxo-benz[de]isoquinolin-2-yl)ethyl]piperazin-1-yl]propyl}-oxy-(11aS)-1,2,3,11a tetrahydro-5H-pyrrolo[2,1-c][1,4]benzodiazepin-5-one of the structural formula

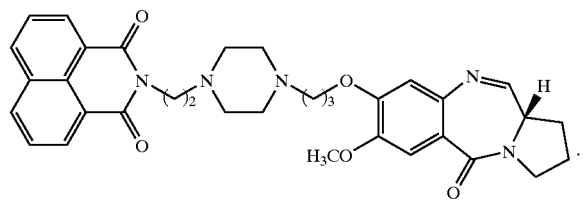

5. 7-Methoxy-8-{4-[4-[2-(1,3-dioxo-benz[de]isoquinolin-2-yl)ethyl]piperazin-1-yl]butyl}-oxy-(11aS)-1,2,3,11a tetrahydro-5H-pyrrolo[2,1-c][1,4]benzodiazepin-5-one of the structural formula

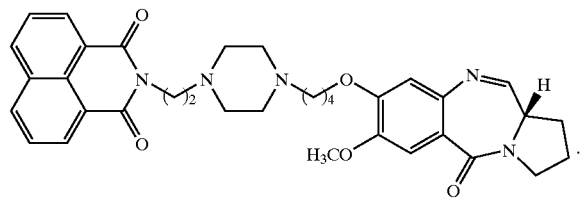

6. 7-Methoxy-8-{3-[4-[3-(1,3-dioxo-benz[de]isoquinolin-2-yl)propyl]piperazin-1-yl]propyl}-oxy-(11aS)-1,2,3, 11a tetrahydro-5H-pyrrolo[2,1-c][1,4]benzodiazepin-5-one of the structural formula 7. 7-Methoxy-8-{4-[4-[4-(1,3-dioxo-benz[de]isoquinolin-2-yl)butyl]piperazin-1-yl]butyl}-oxy-(11aS)-1,2,3,1a tetrahydro-5H-pyrrolo[2,1-c][1,4]benzodiazepin-5-one of the structural formula

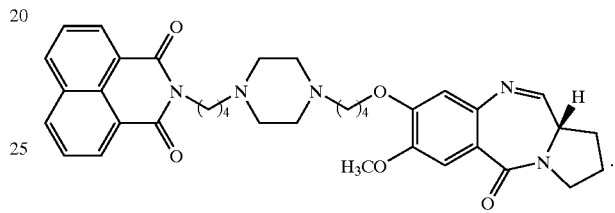

8. 7-Methoxy-8-{4-[4-[2-(1,3-dioxo-benz[de]isoquinolin-2-yl)propyl]piperazin-1-yl]butyl}-oxy-(11aS)-1,2,3,11a tetrahydro-5H-pyrrolo[2,1-c][1,4]benzodiazepin-5-one of the structural formula

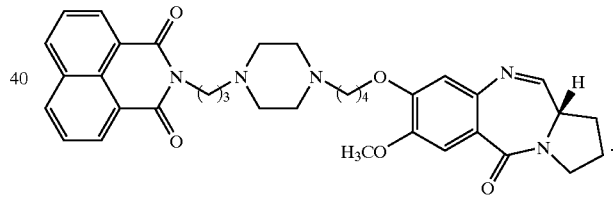

9. 7-Methoxy-8-{3-[4-[2-(1,3-dioxo-benz[de]isoquinolin-2-yl)butyl]piperazin-1-yl]propyl}-oxy-(11aS)-1,2,3,11a tetrahydro-5H-pyrrolo[2,1-c][1,4]benzodiazepin-5-one of the structural formula

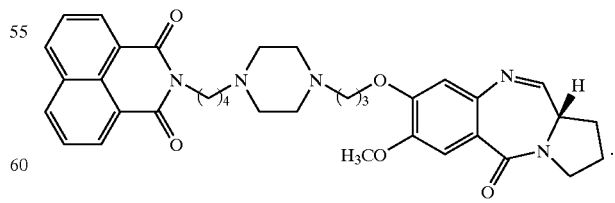

10. 7-Methoxy-8-{3-[4-[3-(1,3-dioxo-benz[de]isoquinolin-2-yl)propyl]piperazin-1-yl]ethyl}-oxy-(11aS)-1,2,3,11a tetrahydro-5H-pyrrolo[2,1-c][1,4]benzodiazepin-5-one of the structural formula

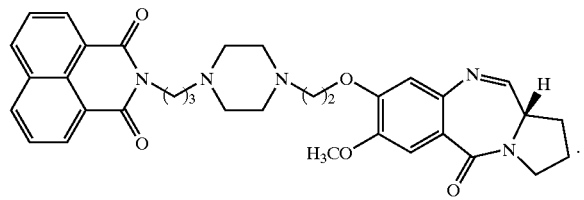

11. A process for the preparation of a compound of formula VIII

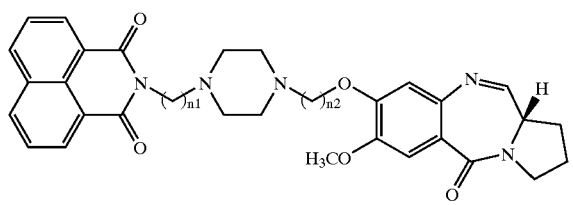

where $n_1$ is 2, 3, or 4, and $n_2$ is 2, 3, or 4, which comprises the steps of:

a) reacting (2S)-N-[4-hydroxy-5-methoxy-2-nitrobenzoyl]pyrrolidine-2-carboxaldehyde diethyl thioacetal of formula IV

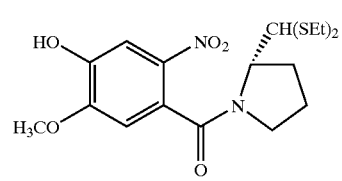

with a dibromoalkane in an aprotic water miscible organic solvent in the presence of a mild inorganic base at reflux temperature for a period of 48 hours, b) isolating 2S-N-[4-(n-bromo alkoxy)-5-methoxy-2-nitrobenzoyl]pyrrolidine-2-carbaxaldehyde diethyl thioacetal of formula V;

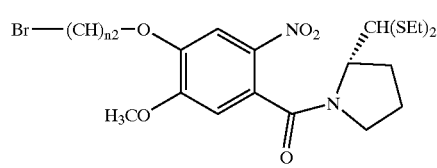

reacting the compound of formula V with piperazine attached naphthalimide in presence of a mild inorganic base;

c) isolating a compound of formula VI,

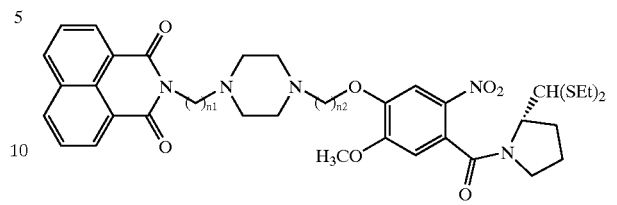

and reducing it with $SnCl_2 \cdot 2H_2O$ in the presence of organic solvent at a reflux temperature to obtain a compound of formula VIII

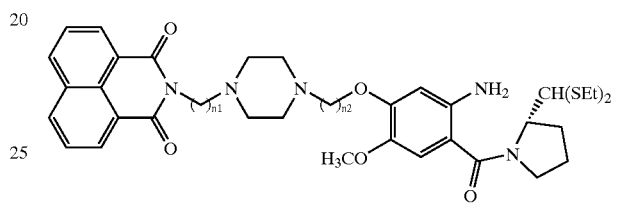

and d) reacting the compound of formula VII with a deprotecting agent to obtain a compound of formula VIII wherein n is as defined above.

12. A method for the treatment of lung, colon or cervical cancer in a human comprising administering to the human a compound of formula VIII

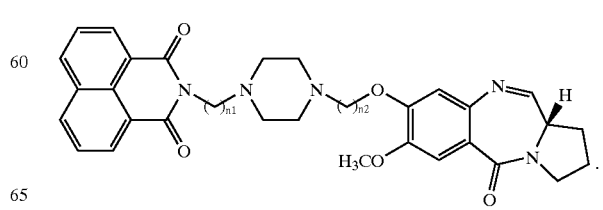

where $n_1$ is 2, 3 or 4 and $n_2$ is 2, 3 or 4 or a pharmaceutically acceptable salt thereof; and a pharmaceutically acceptable additive.

13. A pharmaceutical composition comprising a pharmaceutically effective amount of a compound of formula VIII where $n_1$ is 2, 3 or 4, and $n_2$ is 2, 3 or 4 and a pharmaceutically acceptable excipient

14. A pharmaceutical composition comprising a pharmaceutically effective amount of 7-Methoxy-8-{2-[4-[2-(1,3-dioxo-benz[de]isoquinolin-2-yl)alkyl] piperazin-1-yl]alkyl}-oxy-(11aS)-1,2,3,11a tetrahydro-5H-pyrrolo[2,1-c][1,4]benzodiazepin-5-one of formula VIII were $n_1$ is 2, 3 or 4 and $n_2$ is 2, 3 or 4 and a pharmaceutically acceptable excipient

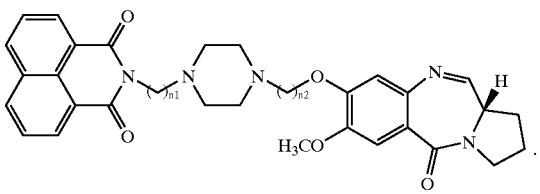

VIII

15. A pharmaceutical composition comprising a pharmaceutically effective amount of 7-Methoxy-8-{2-[4-[2-(1,3-dioxo-benz[de]isoquinolin-2-yl)ethyl] piperazin-1-yl]ethyl}-oxy-(11aS)-1,2,3,11a tetrahydro-5H-pyrrolo[2,1-c][1,4]benzodiazepin-5-one of the formula

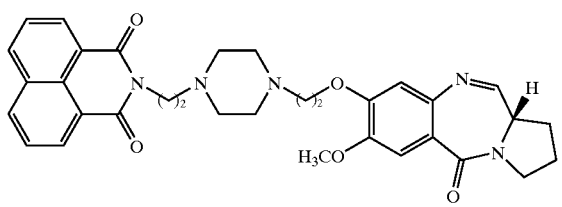

and a pharmaceutically acceptable excipient.

16. A pharmaceutical composition comprising a pharmaceutically effective amount of 7-Methoxy-8-{3-[4-[2-(1,3-dioxo-benz[de]isoquinolin-2-yl)ethyl] piperazin-1-yl]propyl}-oxy-(11aS)-1,2,3,11a tetrahydro-5H-pyrrolo[2,1-c][1,4]benzodiazepin-5-one of the formula

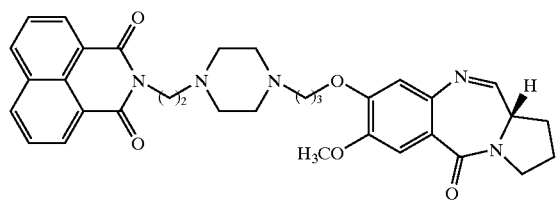

and a pharmaceutically acceptable excipient.

17. A pharmaceutical composition comprising a pharmaceutically effective amount of 7-Methoxy-8-{4-[4-[2-(1,3-dioxo-benz[de]isoquinolin-2-yl)ethyl] piperazin-1-yl]butyl}-oxy-(11aS)-1,2,3,11a tetrahydro-5H-pyrrolo[2,1-c][1,4]benzodiazepin-5-one of the formula

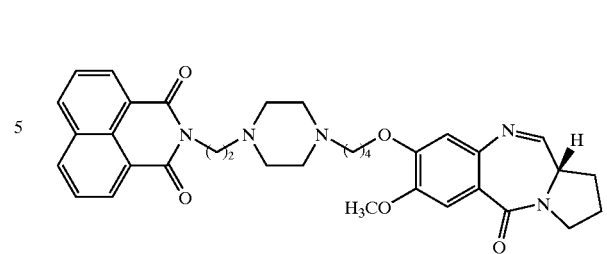

and a pharmaceutically acceptable excipient.

18. A pharmaceutical composition comprising a pharmaceutically effective amount of 7-Methoxy-8-{3-[4-[3-(1,3-dioxo-benz[de]isoquinolin-2-yl)propyl] piperazin-1-yl]propyl}-oxy-(11aS)-1,2,3,11a tetrahydro-5H-pyrrolo[2,1-c][1,4] benzodiazepin-5-one of the formula

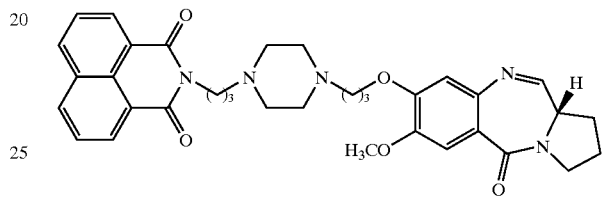

and a pharmaceutically acceptable excipient.

19. A pharmaceutical composition comprising a pharmaceutically effective amount of 7-Methoxy-8-{4-[4-[4-(1,3-dioxo-benz[de]isoquinolin-2-yl)butyl] piperazin-1-yl]butyl}-oxy-(11aS)-1,2,3,11a tetrahydro-5H-pyrrolo[2,1-c][1,4]benzodiazepin-5-one of the formula

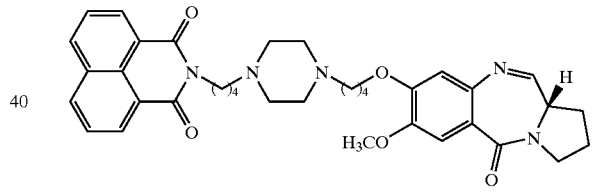

and a pharmaceutically acceptable excipient.

20. A pharmaceutical composition comprising a pharmaceutically effective amount of 7-Methoxy-8-{4-[4-[2-(1,3-dioxo-benz[de]isoquinolin-2-yl)propyl] piperazin-1-yl]butyl}-oxy-(11aS)-1,2,3,11a tetrahydro-5H-pyrrolo[2,1-c][1,4]benzodiazepin-5-one of the formula

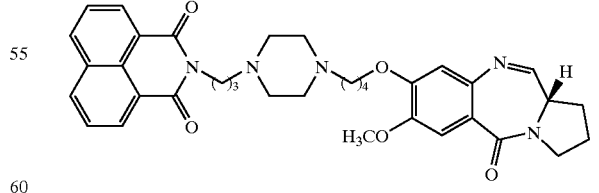

and a pharmaceutically acceptable excipient.

21. A pharmaceutical composition comprising a pharmaceutically effective amount of 7-Methoxy-8-{3-[4-[2-(1,3-dioxo-benz[de]isoquinolin-2-yl)butyl] piperazin-1-yl]propyl}-oxy-(11aS)-1,2,3,11a tetrahydro-5H-pyrrolo[2,1-c][1,4] benzodiazepin-5-one of the formula

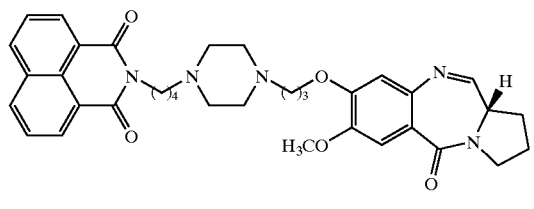
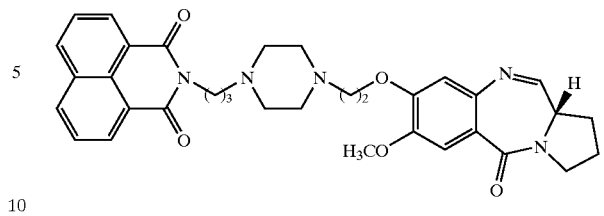
and a pharmaceutically acceptable excipient.
22. A pharmaceutical composition comprising a pharmaceutically effective amount of 7-Methoxy-8-{3-[4-[3-(1,3-dioxo-benz[de]isoquinolin-2-yl)propyl] piperazin-1-yl] ethyl}-oxy-(11aS)-1,2,3,11a tetrahydro-5H-pyrrolo[2,1-c][1,4]benzodiazepin-5-one of the formula
and a pharmaceutically acceptable excipient.
* * * * *